(12) United States Patent
Ikeda et al.

(10) Patent No.: US 11,331,255 B2
(45) Date of Patent: May 17, 2022

(54) COMPOSITION

(71) Applicant: AJINOMOTO CO., INC., Tokyo (JP)

(72) Inventors: Naoaki Ikeda, Kawasaki (JP); Naoya Yamato, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 158 days.

(21) Appl. No.: 16/690,482

(22) Filed: Nov. 21, 2019

(65) Prior Publication Data

US 2020/0085712 A1    Mar. 19, 2020

Related U.S. Application Data

(63) Continuation of application No. PCT/JP2018/019572, filed on May 22, 2018.

(30) Foreign Application Priority Data

May 23, 2017   (JP) .............................. JP2017-101892

(51) Int. Cl.
| | | |
|---|---|---|
| *A61K 8/44* | (2006.01) | |
| *A61K 8/36* | (2006.01) | |
| *A61Q 19/10* | (2006.01) | |
| *A61K 8/19* | (2006.01) | |
| *A61K 8/20* | (2006.01) | |
| *A61K 8/34* | (2006.01) | |
| *A61K 8/362* | (2006.01) | |
| *A61K 8/73* | (2006.01) | |

(52) U.S. Cl.
CPC ................. *A61K 8/44* (2013.01); *A61K 8/19* (2013.01); *A61K 8/20* (2013.01); *A61K 8/345* (2013.01); *A61K 8/361* (2013.01); *A61K 8/362* (2013.01); *A61K 8/731* (2013.01); *A61K 8/737* (2013.01); *A61Q 19/10* (2013.01)

(58) Field of Classification Search
CPC .................................... A61K 8/44; A61K 8/361
See application file for complete search history.

(56) References Cited

U.S. PATENT DOCUMENTS

| | | | | |
|---|---|---|---|---|
| 5,559,092 | A * | 9/1996 | Gibson ..................... | A61K 8/44 514/20.7 |
| 2004/0077518 | A1* | 4/2004 | Nishikawa ............. | C11D 17/06 510/499 |
| 2004/0234486 | A1* | 11/2004 | Hashimoto ........... | A61K 8/8152 424/70.16 |
| 2005/0100572 | A1* | 5/2005 | Hatajima ................ | A61K 8/28 424/401 |
| 2006/0062751 | A1* | 3/2006 | Sato ....................... | A61Q 19/10 424/70.22 |
| 2006/0239952 | A1* | 10/2006 | Hattori .................... | A61K 8/64 424/70.14 |
| 2012/0269875 | A1* | 10/2012 | Tamura .................. | C08G 77/38 424/401 |
| 2014/0187649 | A1* | 7/2014 | Tamura .................... | A61K 8/06 514/772 |
| 2014/0193353 | A1* | 7/2014 | Tamura .................. | C08G 77/46 424/78.02 |
| 2014/0364394 | A1* | 12/2014 | Tamura .................... | A61Q 5/02 514/63 |
| 2015/0250882 | A1* | 9/2015 | Reslow ................ | A61K 47/183 514/11.4 |
| 2016/0120768 | A1 | 5/2016 | Morioka et al. | |
| 2016/0235850 | A1* | 8/2016 | Hattori .................. | A61Q 19/10 |
| 2018/0000709 | A1 | 1/2018 | Yumioka et al. | |
| 2020/0085712 | A1* | 3/2020 | Ikeda ..................... | A61K 8/361 |

FOREIGN PATENT DOCUMENTS

| | | |
|---|---|---|
| CN | 106398905 A | 2/2017 |
| JP | 4-149125 A | 5/1992 |
| JP | 11-323379 A | 11/1999 |
| JP | 2000-143497 A | 5/2000 |
| JP | 2001-31993 A | 2/2001 |
| JP | 2002-20267 A | 1/2002 |
| JP | WO 2004/061060 A1 | 7/2004 |
| JP | 2006-96725 A | 4/2006 |
| JP | 2008-100921 A | 5/2008 |
| JP | 2008-273910 A | 11/2008 |
| JP | 2010-202760 A | 9/2010 |
| JP | 2013-224275 A | 10/2013 |
| JP | 2013-230987 A | 11/2013 |
| JP | 2014-218465 A | 11/2014 |
| JP | 2015-17245 A | 1/2015 |
| JP | 2015-74696 A | 4/2015 |
| JP | 2016-17118 A | 2/2016 |
| JP | 2016-169190 A | 9/2016 |
| JP | 2016169190 A * | 9/2016 |
| JP | 2018-9146 A | 1/2018 |
| WO | WO 2005/033255 A1 | 4/2005 |
| WO | WO 2012/063973 A1 | 5/2012 |
| WO | WO 2015/064678 A1 | 5/2015 |

OTHER PUBLICATIONS

JP 2016. Akimoto et al. (2016). Eng. Translation (Year: 2021).*
International Search Report dated Jul. 10, 2018 in PCT/JP2018/019572 (with English translation), 6 pages.
"Main Fatty Acid Composition of Fat and Oils" Soap Encyclopedia, Retrieved from the Internet: URL:http://www.live-science.com/honkan/soap/soapchemistry03.html, Dec. 5, 2012, 1 page.

* cited by examiner

*Primary Examiner* — Nicole M. Buie-Hatcher
*Assistant Examiner* — M. Reza Asdjodi
(74) *Attorney, Agent, or Firm* — Oblon, McClelland, Maier & Neustadt, L.L.P.

(57) ABSTRACT

Provided is a composition containing the following components (A), (B) and (C) and suppressing formation of scum during cleansing, wherein a weight ratio of (A)/(B) is 0.2-5 and a weight ratio of ((A)+(B))/(C) is 0.01-10:

(A) N-lauroyl glycine or a salt thereof
(B) N-myristoyl glycine or a salt thereof
(C) N-acyl acidic amino acid having an acyl group having 8 to 24 carbon atoms, or a salt thereof.

20 Claims, No Drawings

COMPOSITION

CROSS REFERENCES TO RELATED APPLICATIONS

This application is a continuation of International Patent Application No. PCT/JP2018/019572, filed on May 22, 2018, and claims priority to Japanese Patent Application No. 2017-101892, filed on May 23, 2017, all of which are incorporated herein by reference in their entireties.

BACKGROUND OF THE INVENTION

Field of the Invention

The present invention relates to a composition with less formation of scum during cleansing.

Discussion of the Background

In Japan and Asia, as facial or whole body cleansing agents used mainly in bathrooms, cleansing agents providing a refreshing feeling and abundant foam are preferred to cover a large area of the body and create a refreshing feeling after washing. As a component that imparts a refreshing feeling, scum is known which is an insoluble material between metal ions and a cleansing agent. On the other hand, it is known that scum, which is an insoluble matter generated from metal ions contained in tap water and cleansing agents, is generated during cleansing and leads to bathroom dirt. To easily maintain the cleanliness and aesthetic appearance of the bathroom used every day, therefore, a cleansing agent that hardly forms scum is desired. In addition, since a large amount of drainage is required to wash away the formed scum, an environmentally friendly cleansing agent less likely to form scum is demanded in the world.

As a method for suppressing scum, suppression of scum by acyl amino acid has been proposed. However, it concerns use of a bath agent effective for improving water quality and maintaining a bathtub and a bath boiler (patent document 1). Since the use is not for a body cleansing agent, the problem in terms of the refreshing feeling and the amount of foam has not been solved.

As a body cleansing agent that creates a refreshing feeling, a cleansing composition that combines a higher fatty acid salt with an acyl amino acid and a cationic polymer has been proposed. However, since a higher fatty acid salt is used, even though the refreshing feeling and foam performance during cleansing satisfy the demands, the suppression of scum did not always exhibit a sufficient effect (patent document 2).

Also, the use of acyl glycine as a body cleansing agent has been proposed (patent document 3). Since acyl glycine has a structure relatively similar to fatty acid, it shows foam performance and texture close to those of fatty acid. However, similar to fatty acid, it easily forms a divalent metal salt and may cause bathroom stains.

DOCUMENT LIST

Patent documents patent document 1: JP-A-4-149125
patent document 2: JP-A-2015-74696
patent document 3: JP-A-2014-218465

SUMMARY OF THE INVENTION

Problems to be Solved by the Invention

The present invention aims to provide a composition with less formation of scum during cleansing.

Means of Solving the Problems

The present inventors have conducted intensive studies in an attempt to solve the above-mentioned problems, and found that formation of scum during cleansing is reduced by affording a composition having a particular mixing ratio of N-lauroyl glycine or a salt thereof, N-myristoyl glycine or a salt thereof, and particular N-acyl acidic amino acid or a salt thereof. Furthermore, they have found that a composition showing good foam removal and superior in the sense of use can be obtained by adding a fatty acid to the composition, which resulted in the completion of the present invention.

Therefore, the present invention provides the following.
[1] A composition comprising the following components (A), (B) and (C), wherein a weight ratio of (A)/(B) is 0.2-5 and a weight ratio of ((A)+(B))/(C) is 0.01-10:
(A) N-lauroyl glycine or a salt thereof
(B) N-myristoyl glycine or a salt thereof
(C) N-acyl acidic amino acid having an acyl group having 8 to 24 carbon atoms, or a salt thereof.
[2] The composition of [1] further comprising component (D) fatty acid having 6 to 24 carbon atoms or a salt thereof.
[3] The composition of [2] wherein (D) is at least one selected from the group consisting of octanoic acid, decanoic acid, lauric acid, myristic acid, palmitic acid, stearic acid, a sodium salt thereof, a potassium salt thereof and a triethanolamine salt thereof.
[4] The composition of [1] or [2], wherein the acidic amino acid of (C) is glutamic acid or aspartic acid.
[5] The composition of any of [1] to [4], wherein (C) N-acyl acidic amino acid salt is a salt with at least one selected from the group consisting of sodium, potassium and triethanolamine.
[6] The composition of any of [1] to [5], wherein (C) is at least one selected from the group consisting of N-lauroyl glutamic acid, N-myristoyl glutamic acid, N-cocoyl glutamic acid, sodium salts thereof, potassium salts thereof and triethanolamine salts thereof.
[7] The composition of any of [1] to [6], wherein (A) N-lauroyl glycine salt is a salt with at least one selected from the group consisting of sodium, potassium and triethanolamine.
[8] The composition of any of [1] to [7], wherein (B) N-myristoyl glycine salt is a salt with at least one selected from the group consisting of sodium, potassium and triethanolamine.
[9] The composition of any of [2] to [8], wherein a weight ratio of ((A)+(B)+(C))/(D) is 0.02 or more.
[10] The composition of any of [1] to [9] further comprising component (E) N-lauroylglycyl glycine or a salt thereof.
[11] The composition of any of [1] to [10] further comprising component (F) N-myristoylglycyl glycine or a salt thereof.
[12] The composition of any of [1] to [11] further comprising component (G) N-lauroylglutamyl glutamic acid or a salt thereof.
[13] The composition of any of [1] to [12] further comprising component (H) N-acyl arginine or a salt thereof.

[14] A cleansing composition comprising the composition of any of [2] to [13].

[15] The composition of [14] wherein the aforementioned (D) is contained at not less than 0.1 wt % and not more than 50 wt % relative to the whole cleansing composition.

[16] The composition of [14] wherein the aforementioned (D) is contained at not less than 0.5 wt % and not more than 30 wt % relative to the whole cleansing composition.

[17] The composition of any of [1] to [13] wherein a weight ratio of (A)/(B) is 0.3-3.5 and a weight ratio of ((A)+(B))/(C) is 0.5-4.

[18] The composition of any of [1] to [13] and [17] wherein a total weight of (A)-(C) is 15-40 wt % relative to the whole composition.

[19] A cleansing composition comprising the composition of any of [1] to [13], [17] and [18].

Effect of the Invention

When the composition of the present invention is used for cleansing, formation of scum becomes small, bathroom dirt and the like are less and a large amount of water for washing away scum is not necessary, and thus the composition can contribute to the environment.

According to the present invention, a cleansing agent showing good foam removal can be provided which can be rinsed off quickly and is superior in usability.

DETAILED DESCRIPTION OF THE PREFERRED EMBODIMENTS

The present invention relates to a composition containing components (A) N-lauroyl glycine or a salt thereof, (B) N-myristoyl glycine or a salt thereof and (C) N-acyl acidic amino acid having an acyl group having 8 to 24 carbon atoms, or a salt thereof (hereinafter to be also respectively referred to as (A), (B) and (C)) at a particular ratio (hereinafter sometimes to be abbreviated as the composition of the present invention).

As a salt of (A) N-lauroyl glycine, alkali metal salts such as lithium salt, sodium salt, potassium salt and the like; alkaline earth metal salts such as calcium salt, magnesium salt and the like; alkanolamine salts such as monoethanolamine salt, diethanolamine salt, triethanolamine (TEA) salt and the like; ammonium salt; and salt of basic organic substance and the like can be mentioned. Of these, alkali metal salt and alkanolamine salt are preferable, and sodium salt, potassium salt and triethanolamine salt are more preferable, for suppressing the formation of scum. The N-lauroyl glycine and a salt thereof may each be used alone, or two or more kinds thereof may be used in a mixture at any ratio.

(A) may be in the form of a salt, which is obtained by adding, when the composition of the present invention is prepared, N-lauroyl glycine together with a substance (e.g., sodium hydroxide, potassium hydroxide, TEA etc.) that forms the above-mentioned salts, thus performing neutralization. The N-lauroyl glycine and a salt thereof may each be used alone, or two or more kinds thereof may be used in a mixture at any ratio.

In the present invention, the "scum" means an insoluble matter which is a chelate of divalent metal ions such as calcium and the like in water and a surfactant.

As a salt of (B) N-myristoyl glycine, alkali metal salts such as lithium salt, sodium salt, potassium salt and the like; alkaline earth metal salts such as calcium salt, magnesium salt and the like; alkanolamine salts such as monoethanolamine salt, diethanolamine salt, triethanolamine (TEA) salt and the like; ammonium salt; and salt of basic organic substance and the like can be mentioned. Of these, alkali metal salt and alkanolamine salt are preferable, and sodium salt, potassium salt, triethanolamine salt are more preferable for suppressing the formation of scum. The N-myristoyl glycine and a salt thereof may each be used alone, or two or more kinds thereof may be used in a mixture at any ratio.

(B) may be in the form of a salt, which is obtained by adding, when the composition of the present invention is prepared, N-myristoyl glycine together with a substance (e.g., sodium hydroxide, potassium hydroxide, TEA etc.) that forms the above-mentioned salts, thus performing neutralization.

As (C) N-acyl acidic amino acid or a salt thereof, any of D form, L form and DL form can be used. The N-acyl acidic amino acid and a salt thereof may each be used alone, or two or more kinds thereof may be used in a mixture at any ratio.

The acyl group of (C) N-acyl acidic amino acid is an acyl group induced from fatty acid having 8 to 24 carbon atoms, and an acyl group induced from fatty acid having 8 to 22 carbon atoms is preferable, and an acyl group induced from fatty acid having 8 to 18 carbon atoms is more preferable. Examples of the acyl group include an acyl group induced from lauric acid, myristic acid, palmitic acid, stearic acid, oleic acid, isostearic acid or the like, a mixture thereof such as beef tallow fatty acid, coconut oil fatty acid, palm kernel oil fatty acid and the like can be mentioned, an acyl group induced from lauric acid, myristic acid or coconut oil fatty acid is preferable, and an acyl group induced from lauric acid or coconut oil fatty acid is more preferable.

While the acidic amino acid of (C) is not particularly limited as long as it is an acidic amino acid, examples thereof include glutamic acid, aspartic acid and the like, and glutamic acid and aspartic acid are preferable.

As a salt of N-acyl acidic amino acid, alkali metal salts such as lithium salt, sodium salt, potassium salt and the like; alkaline earth metal salts such as calcium salt, magnesium salt and the like; alkanolamine salts such as monoethanolamine salt, diethanolamine salt, triethanolamine (TEA) salt and the like; ammonium salt; and salt of basic organic substance and the like can be mentioned. Of these, alkali metal salt and alkanolamine salt are preferable, and sodium salt, potassium salt, triethanolamine salt are more preferable, for suppressing the formation of scum. The N-acyl acidic amino acid and a salt thereof may each be used alone, or two or more kinds thereof may be used in a mixture at any ratio.

(C) may be in the form of a salt, which is obtained by adding, when the composition of the present invention is prepared, N-acyl acidic amino acid together with a substance (e.g., sodium hydroxide, potassium hydroxide, TEA etc.) that forms the above-mentioned salts, thus performing neutralization. Furthermore, (C) may contain unneutralized N-acyl acidic amino acid.

Specific examples of the N-acyl acidic amino acid salt to be used in the present invention include monosodium salt, monopotassium salt, triethanolamine salt and the like of N-lauroyl glutamic acid, N-myristoyl glutamic acid, N-cocoyl (coconut oil fatty acid acyl) glutamic acid, N-lauroyl aspartic acid, N-myristoyl aspartic acid or N-cocoyl aspartic acid. One kind of these may be used or two or more kinds thereof may be used in a mixture. Of these, a sodium salt, a potassium salt or a triethanolamine salt of N-lauroyl glutamic acid, N-myristoyl glutamic acid or N-cocoyl glutamic acid, or a mixture thereof is preferable, and a potassium salt, a sodium salt or a triethanolamine salt of N-lauroyl glutamic acid or N-cocoyl glutamic acid, or a mixture thereof is preferable.

The composition of the present invention is characterized in that a weight ratio of (A)/(B) is 0.2-5. The weight ratio of (A)/(B) is preferably 0.3-3.5, more preferably 0.3-2.3. A composition superior in the sense of use and the like can be provided when the weight ratio is within these ranges.

The composition of the present invention is also characterized in that a weight ratio of ((A)+(B))/(C) is 0.01-10.0. The weight ratio of ((A)+(B))/(C) is preferably 0.1 or more, more preferably one or more, preferably not more than 9, more preferably not more than 4, further preferably not more than 3.5, particularly preferably not more than 2.5. Specifically, the weight ratio of ((A)+(B))/(C) is generally 0.01-10, preferably 0.1-9, more preferably 0.1-4, further preferably 0.5-4, particularly preferably 0.5-3.5.

Within this range, a composition superior in the sense of use and quick foam removal and with suppressed formation of scum can be provided when the weight ratio is within these ranges.

As (A), (B) and (C) in the present invention, synthesized products and commercially available products can be used.

The composition of the present invention preferably further contains component (D) fatty acid having 6 to 24 carbon atoms or a salt thereof (hereinafter to be also referred to as (D)) from the aspect of quick foam removal.

The fatty acid having 6 to 24 carbon atoms may be saturated or unsaturated, a fatty acid having 6 to 18 carbon atoms is preferable, and a fatty acid having 8 to 18 carbon atoms is more preferable.

Specific examples of saturated fatty acid the include straight chain saturated fatty acids such as hexanoic acid (caproic acid), heptanoic acid, octanoic acid (caprylic acid), nonanoic acid, decanoic acid (capric acid), dodecanoic acid (lauric acid), tetradecanoic acid (myristic acid), pentadecanoic acid, hexadecanoic acid (palmitic acid), heptadecanoic acid, octadecanoic acid (stearic acid), icosanoic acid (arachidic acid), henicosylic acid, docosanoic acid (behenic acid), tetracosanoic acid (lignoceric acid) and the like and branched chain saturated fatty acids such as isostearic acid, 2-hexyldecanoic acid, 2-ethylhexanoic acid, isononanoic acid, 12-hydroxystearic acid and the like. Among these, octanoic acid, decanoic acid, lauric acid, myristic acid, palmitic acid, stearic acid are preferable, lauric acid, myristic acid, palmitic acid, stearic acid are more preferable.

As the unsaturated fatty acid, 9-hexadecenoic acid (pulmitoleic acid), cis-9-octadecenoic acid (oleic acid), 11-octadecenoic acid (vaccenic acid)cis,cis-9,12-octadecadienoic acid (linoleic acid), 9,12,15-octadecatrienoic acid ((9,12,15)-linolenic acid), 5,8,11,14-eicosatetraenoic acid (arachidonic acid) and the like can be mentioned.

As a salt of fatty acid having 6 to 24 carbon atoms, alkali metal salts such as lithium salt, sodium salt, potassium salt and the like; alkaline earth metal salts such as calcium salt, magnesium salt and the like; alkanolamine salts such as monoethanolamine salt, diethanolamine salt, triethanolamine (TEA) salt and the like; ammonium salt; and salt of basic organic substance and the like can be mentioned. From the above-mentioned aspects, alkali metal salt and alkanolamine salt are preferable, and sodium salt, potassium salt, triethanolamine are more preferable, and potassium salt is particularly preferable. These fatty acid having 6 to 24 carbon atoms and a salt thereof may each be used alone, or two or more kinds thereof may be used in a mixture at any ratio.

In the present invention, the weight ratio of ((A)+(B)+(C))/(D) is generally not less than 0.02, preferably not less than 0.05, and more preferably not less than 1, from the aspect of quick foam removal. It is generally not more than 300, preferably not more than 100, more preferably not more than 50, further preferably not more than 10.

From the aspect of quick foam removal, the content of (D) is generally not less than 0.01 wt %, preferably not less than 0.5 wt %, more preferably not less than 1 wt % and generally not more than 50 wt %, preferably not more than 30 wt %, more preferably not more than 20 wt %, relative to the whole composition.

The composition of the present invention may further contain component (E) N-lauroylglycyl glycine or a salt thereof (hereinafter to be also referred to as (E)) from the aspect of improving scum adhesive property.

As a salt of N-lauroylglycyl glycine, alkali metal salts such as lithium salt, sodium salt, potassium salt and the like; alkaline earth metal salts such as calcium salt, magnesium salt and the like; alkanolamine salts such as monoethanolamine salt, diethanolamine salt, triethanolamine (TEA) salt and the like; ammonium salt; and salt of basic organic substance and the like can be mentioned. From the above-mentioned aspects, alkali metal salt and alkanolamine salt are preferable, and sodium salt, potassium salt and triethanolamine salt are more preferable, and potassium salt is particularly preferable. The N-lauroylglycyl glycine and a salt thereof may each be used alone, or two or more kinds thereof may be used in a mixture at any ratio.

In the composition of the present invention, the weight ratio of (A) and (E) is generally 99.99:0.01-0.01:99.99, preferably 90:10-10:90, more preferably 90:10-30:70.

The content of (E) is generally not less than 0.0001 wt % and not more than 10 wt %, preferably not less than 0.2 wt % and not more than 8 wt %, more preferably not less than 0.3 wt % and not more than 5 wt %, relative to the whole composition.

The composition of the present invention may further contain component (F) N-myristoylglycyl glycine or a salt thereof (hereinafter to be also referred to as (F)) from the aspect of improving foam removal property.

As a salt of N-myristoylglycyl glycine, alkali metal salts such as lithium salt, sodium salt, potassium salt and the like; alkaline earth metal salts such as calcium salt, magnesium salt and the like; alkanolamine salts such as monoethanolamine salt, diethanolamine salt, triethanolamine (TEA) salt and the like; ammonium salt; and salt of basic organic substance and the like can be mentioned. From the above-mentioned aspects, alkali metal salt and alkanolamine salt are preferable, and sodium salt, potassium salt and triethanolamine salt are more preferable, and potassium salt is particularly preferable. The N-myristoylglycyl glycine and a and a salt thereof may each be used alone, or two or more kinds thereof may be used in a mixture at any ratio.

In the composition of the present invention, the weight ratio of (B) and (F) is generally 99.99:0.01-0.01:99.99, preferably 90:10-10:90, more preferably 90:10-30:70.

The content of (F) is generally not less than 0.0001 wt % and not more than 10 wt %, preferably not less than 0.2 wt % and not more than 8 wt %, more preferably not less than 0.3 wt % and not more than 5 wt %, relative to the whole composition.

The composition of the present invention may further contain component (G) N-lauroylglutamyl glutamic acid or a salt thereof (hereinafter to be also referred to as (G)) from the aspect of improving foam removal property.

As a salt of N-lauroylglutamyl glutamic acid, alkali metal salts such as lithium salt, sodium salt, potassium salt and the like; alkaline earth metal salts such as calcium salt, magnesium salt and the like; alkanolamine salts such as monoethanolamine salt, diethanolamine salt, triethanolamine (TEA) salt and the like; ammonium salt; and salt of basic organic substance and the like can be mentioned. From the above-mentioned aspects, alkali metal salt and alkanolamine salt are preferable, and sodium salt, potassium salt, triethanolamine are more preferable, and potassium salt is particularly preferable. The N-lauroylglutamyl glutamic acid and a salt thereof may each be used alone, or two or more kinds thereof may be used in a mixture at any ratio.

In the composition of the present invention, the weight ratio of (C) and (G) is generally 99.99:0.01-0.01:99.99, preferably 95:5-10:90, more preferably 95:5-30:70.

The content of (G) is generally not less than 0.0001 wt % and not more than 10 wt %, preferably not less than 0.2 wt % and not more than 8 wt %, more preferably not less than 0.3 wt % and not more than 5 wt %, relative to the whole composition.

The composition of the present invention may further contain component (H) N-acyl arginine or a salt thereof (hereinafter to be also referred to as (H)) from the aspects of imparting scum hydrophilicity, foaming, improving foam quality.

As (H) N-acyl arginine or a salt thereof in the present invention, any of D form, L form and DL form can be used. The acyl arginine and a salt thereof may each be used alone, or two or more kinds thereof may be used in a mixture at any ratio.

The acyl group of (H) N-acyl arginine or a salt thereof in the present invention is an acyl group induced from fatty acid having 8 to 24 carbon atoms, and an acyl group induced from fatty acid having 8 to 16 carbon atoms is preferable, and an acyl group induced from fatty acid having 10 to 12 carbon atoms is more preferable. Examples of the acyl group include an acyl group induced from lauric acid, myristic acid, palmitic acid, stearic acid or the like, a mixture thereof such as beef tallow fatty acid, coconut oil fatty acid, palm kernel oil fatty acid and the like can be mentioned, an acyl group induced from lauric acid or myristic acid is preferable, and an acyl group induced from lauric acid is more preferable.

As a salt of N-acyl arginine, alkali metal salts such as lithium salt, sodium salt, potassium salt and the like; alkaline earth metal salts such as calcium salt, magnesium salt and the like; alkanolamine salts such as monoethanolamine salt, diethanolamine salt, triethanolamine (TEA) salt and the like; ammonium salt; and salt of basic organic substance and the like can be mentioned. Of these, sodium salt, potassium salt and alkanolamine salt are preferable from the aspect of high solubility, and sodium salt is more preferable from the aspect of price acceptability. The N-acyl arginine and a salt thereof may each be used alone, or two or more kinds thereof may be used in a mixture at any ratio.

(H) N-acyl arginine may be in the form of a salt, which is obtained by adding, when the composition of the present invention is prepared, N-acyl acidic amino acid together with a substance (e.g., sodium hydroxide, potassium hydroxide, TEA etc.) that forms the above-mentioned salts, thus performing neutralization. Furthermore, component (H) N-acyl arginine may contain unneutralized N-acyl acidic amino acid.

Specific examples of the N-acyl arginine to be used in the present invention include lauroyl arginine, myristoyl arginine, decanoylarginine and the like. One kind of these may be used or two or more kinds thereof may be used in a mixture. Among others, a mixture of N-lauroyl arginine is preferable.

From the aspect of dissolution state stability, the content of (H) N-acyl arginine is generally not less than 0.0001 wt % and not more than 5 wt %, preferably not less than 0.01 wt % and not more than 3 wt %, more preferably not less than 0.02 wt % and not more than 3 wt %, relative to the whole composition.

From the aspect of improving handling property at high concentration, the composition of the present invention can be prepared by adding a suitable solvent such that the total content of (A)-(C) is generally 15-40 wt %, preferably 20-35 wt %, more preferably 20-30 wt %, by a method known per se.

From the aspect of improving handling property at high concentration, the composition of the present invention can be prepared by adding a suitable solvent such that the total content of components (A)-(D) is generally 10-45 wt %, preferably 15-40 wt %, more preferably 15-35 wt %, by a method known per se.

In the present invention, a cleansing composition can be obtained solely from the composition of the present invention or by adding various additives generally used as long as the effect of the invention is not inhibited.

For example, starting materials and the like described in various official compendia such as Japanese Standards of Cosmetic Ingredients, Cosmetic Ingredients Codex, Japanese Standard of Quasi-drug Ingredients, the Japanese Pharmacopoeia, Japanese Standards for Pharmaceutical Ingredient, Japan's Specifications and Standards for Food Additives and the like, such as higher alcohols such as cetyl alcohol, stearyl alcohol, behenyl alcohol, isostearyl alcohol, octyldodecanol, oleyl alcohol, myristyl alcohol and the like; higher fatty acids such as hardened beef tallow fatty acid, coconut oil fatty acid, palm oil fatty acid and the like and a salt thereof (excluding fatty acid having 6 to 24 carbon atoms or a salt thereof); moisturizers such as trimethylglycine and the like; surfactants such as anionic surfactant (excluding (A)-(C), salt of (D) and (E) (H) in the present invention), cationic surfactant, amphoteric surfactant, nonionic surfactant and the like; synthetic fats and oils such as vegetable oil, animal fats and oils, natural fat and oil derivatives, mineral fats and oils, lower and higher fatty acid ester and the like; silicone compound; polymer substance; animal and plant extracts; amino acid; nucleic acid; vitamin; enzyme; anti-inflammatory agent; antimicrobial agent; preservative; antioxidant; ultraviolet absorber; chelating agent; antiperspirant; oxidation dye; pH adjuster; pearly sheen agent; and the like can be mentioned.

The composition and the cleansing composition of the present invention can be produced by a method known per se. For example, a mixture of the above-mentioned respective components and other additives are mixed, and the mixture is generally heated at 80-90° C. for 5 min-10 min to uniformly dissolve each component. The obtained composition can be prepared as a cleansing composition in a desired form by a method known per se. For example, each component is uniformly dissolved by heating, which is injected in a mold, solidified by cooling, and dried and matured to give a solid cleansing composition.

Examples of the cleansing composition include shampoo, facial cleanser, body shampoo, hand soap, shaving agent, cleansing agent for kitchen, laundry detergent and the like.

The form of the composition and the cleaning composition of the present invention is not particularly limited, and may be any form, for example, solid, liquid, paste, gel, powder, granule, cream and the like. Of these, liquid, powder or granule is preferable, and liquid is particularly preferable, since it is superior in handling.

From the aspect of quick foam removal, the concentration of (D) in the cleansing composition is generally not less than 0.1 wt %, preferably not less than 0.5 wt %, more preferably not less than 1 wt % and generally not more than 50 wt %, preferably not more than 30 wt %, more preferably not more than 20 wt %, relative to the whole cleansing composition.

The concentrations in the cleansing composition when the cleansing composition is liquid are, for example, total concentration of (A)-(C) generally 1-30 wt %, preferably 3-25 wt %, more preferably 3-20 wt %, total concentration of (A)-(D) generally 1-35 wt %, preferably 3-30 wt %, more preferably 3-25 wt %, relative to the total amount of the cleansing composition.

When the composition of the present invention is a liquid cleansing composition, its pH is generally 5-12, preferably 6-10, more preferably 7-10. A cleansing composition suppressing formation of scum can be provided when the pH is within these ranges.

When the cleansing composition of the present invention is other than a liquid, its pH is defined to be pH of a 10% aqueous solution thereof (25° C.), which is in accordance with the above-mentioned pH ranges.

Other features of the invention will become apparent in the course of the following descriptions of exemplary embodiments which are given for illustration of the invention and are not intended to be limiting thereof.

EXAMPLES

While the present invention is explained in more detail in the following by referring to Examples, the present invention is not limited to these Examples. Unless particularly indicated, % means wt %.

[Preparation 1 of Composition]

Potassium lauroyl glycinate, potassium lauroylglycyl glycinate, potassium myristoyl glycinate, potassium myristoylglycyl glycinate, and potassium lauroyl glutamate were prepared by synthesizing by the Schotten-Baumann method, followed by purification.

(1) Hydrophilicity Test of Scum

The contents of Examples 1-25 and Comparative Examples 1-10 shown in Table 1 were prepared by a conventional method, and then diluted 5-fold with ion exchange water. The diluted product was diluted 100-fold with commercially available hard water (trade name: Contrex, hardness 1,468 mg/L) so as to be 10 g, and weighed in a 30 mL glass vial and used as a sample. The appearance of the sample was evaluated according to the following criteria, and the degree of hydrophilicity and hydrophobicity of the scum was evaluated according to the following criteria. Since the scum having high hydrophilicity is easily adapted to water, it contributes to scum cleaning with less energy.

The results are shown in Table 1. The unit of the compositions shown in Table 1 is wt %.

A: hydrophilic and easily adapted to water: formed scum sinks to bottom of sample container
B: rather hydrophobic and not easily adapted to water: scum is present on liquid surface and lower part of sample container
C: hydrophobic and not easily adapted to water: scum floats on liquid surface (2) Scum Adhesive Property Test The contents of Examples 1-25 and Comparative Examples 1-10 shown in Table 1 were prepared by a conventional method, and then diluted 5-fold with ion exchange water. The diluted product was diluted 100-fold with commercially available hard water (trade name: Contrex, hardness 1,468 mg/L) so as to be 10 g, and weighed in a 30 mL glass vial and used as a sample. The glass vial containing the sample was vigorously shaken up and down and then allowed to stand, and the degree of adhesion of scum to the inner wall of the glass vial was evaluated according to the following criteria, and the degree of scum adhesiveness was evaluated according to the following criteria. The lower the scum adhesiveness, the easier it is for the scum to separate from the solid surface, which contributes to the improvement of scum cleaning performance. The results are shown in Table 1.

A: adhesion of scum to inner wall cannot be visually confirmed
B: adhesion of scum to inner wall can be continued
C: intense adhesion of scum to inner wall can be confirmed (3) Foam Removal Test The contents of Examples 1-25 and Comparative Examples 1-10 shown in Table 1 were prepared by a conventional method, and then diluted 5-fold with ion exchange water. The diluted product was diluted 100-fold with commercially available hard water (trade name: Contrex, hardness 1,468 mg/L) so as to be 10 g, and weighed in a 30 mL glass vial and used as a sample. The glass vial containing the sample was vigorously shaken up and down and then allowed to stand for 15 sec. The amount of foam after standing was visually evaluated according to the following criteria. The smaller the amount of foam, the better the foam removal, thus preventing the foam from staying at the drain outlet and the like, and contributing to the suppression of residual scum. The results are shown in Table 1.

A: foam almost disappear
B: foam less than 5 mm in height remains on liquid surface
C: foam not less than 5 mm in height remains on liquid surface

TABLE 1

|   |   | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 |
|---|---|---|---|---|---|---|---|---|---|---|---|---|---|
| A | potassium lauroyl glycinate | 5.28 | 4.48 | 3.63 | 3.03 | 1.79 | 0.79 | 0.37 | 5.67 | 4.63 | 3.88 | 2.33 | 0.48 |
| B | potassium myristoyl glycinate | 15.83 | 13.45 | 10.90 | 9.08 | 5.38 | 2.36 | 1.10 | 11.51 | 9.40 | 7.88 | 4.72 | 0.98 |
| C | potassium lauroyl glutamate | 3.27 | 6.42 | 9.80 | 12.20 | 17.10 | 21.10 | 22.76 | 6.15 | 9.46 | 11.85 | 16.81 | 22.68 |
| D | potassium laurate | 5.62 | 5.64 | 5.67 | 5.69 | 5.73 | 5.76 | 5.77 | 6.67 | 6.50 | 6.39 | 6.14 | 5.86 |
|   | deionized water | balance | balance | balance | balance | balance | balance | balance | balance | balance | balance | balance | balance |
|   | total | 100 | 100 | 100 | 100 | 100 | 100 | 100 | 100 | 100 | 100 | 100 | 100 |
|   | A/B | 0.33 | 0.33 | 0.33 | 0.33 | 0.33 | 0.33 | 0.33 | 0.49 | 0.49 | 0.49 | 0.49 | 0.49 |
|   | (A + B)/C | 6.45 | 2.80 | 1.48 | 0.99 | 0.42 | 0.15 | 0.06 | 2.80 | 1.48 | 0.99 | 0.42 | 0.06 |
|   | (A + B + C)/D | 4.34 | 4.32 | 4.29 | 4.27 | 4.24 | 4.21 | 4.20 | 3.50 | 3.61 | 3.70 | 3.88 | 4.12 |
|   | scum adhesive property | B | A | A | A | A | A | A | A | A | A | A | A |
|   | foam removal property | A | A | A | A | A | B | B | A | A | A | A | B |

TABLE 1-continued

| | scum hydrophilicity | A | A | A | A | A | A | A | A | A | A | A | A | A |
|---|---|---|---|---|---|---|---|---|---|---|---|---|---|---|
| | | Ex. 13 | Ex. 14 | Ex. 15 | Ex. 16 | Ex. 17 | Ex. 18 | Ex. 19 | Ex. 20 | Ex. 21 | Ex. 22 | Ex. 23 | Ex. 24 | Ex. 25 |
| A | potassium lauroyl glycinate | 7.70 | 6.63 | 5.45 | 4.59 | 2.78 | 0.58 | 9.09 | 7.89 | 6.54 | 5.54 | 3.40 | 6.49 | 5.48 |
| B | potassium myristoyl glycinate | 11.55 | 9.95 | 8.18 | 6.88 | 4.17 | 0.88 | 9.09 | 7.89 | 6.54 | 5.54 | 3.40 | 19.48 | 16.44 |
| C | potassium lauroyl glutamate | 2.98 | 5.93 | 9.18 | 11.56 | 16.56 | 22.61 | 2.82 | 5.64 | 8.82 | 11.17 | 16.21 | 4.03 | 7.84 |
| D | potassium laurate | 7.77 | 7.49 | 7.19 | 6.97 | 6.50 | 5.93 | 9.00 | 8.58 | 8.10 | 7.75 | 6.99 | | 0.23 |
| | deionized water | balance | balance | balance | balance | balance | balance | balance | balance | balance | balance | balance | balance | balance |
| | total | 100 | 100 | 100 | 100 | 100 | 100 | 100 | 100 | 100 | 100 | 100 | 100 | 100 |
| | A/B | 0.67 | 0.67 | 0.67 | 0.67 | 0.67 | 0.67 | 1.00 | 1.00 | 1.00 | 1.00 | 1.00 | 0.33 | 0.33 |
| | (A + B)/C | 6.45 | 2.80 | 1.48 | 0.99 | 0.42 | 0.06 | 6.45 | 2.80 | 1.48 | 0.99 | 0.42 | 6.45 | 2.80 |
| | (A + B + C)/D | 2.86 | 3.00 | 3.17 | 3.31 | 3.62 | 4.06 | 2.33 | 2.50 | 2.70 | 2.87 | 3.29 | | 127.08 |
| | scum adhesive property | B | A | A | A | A | A | B | A | A | A | A | A | A |
| | foam removal property | A | A | A | A | A | B | A | A | A | A | A | C | C |
| | scum hydrophilicity | B | A | A | A | A | A | A | A | A | A | A | A | A |

| | | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 | Comp. Ex. 10 |
|---|---|---|---|---|---|---|---|---|---|---|---|
| A | potassium lauroyl glycinate | 6.10 | 7.60 | 8.78 | 10.29 | | | | 6.16 | 2.93 | 8.68 |
| B | potassium myristoyl glycinate | 18.31 | 15.43 | 13.17 | 10.29 | 10.27 | 13.35 | 7.59 | | | 13.36 |
| C | potassium lauroyl glutamate | | | | | 15.92 | 13.45 | 18.09 | 14.69 | 19.68 | |
| D | potassium laurate | 5.59 | 6.97 | 8.05 | 9.43 | 3.80 | 3.21 | 4.32 | 9.15 | 7.39 | 7.96 |
| | deionized water | balance | balance | balance | balance | balance | balance | balance | balance | balance | balance |
| | total | 100 | 100 | 100 | 100 | 100 | 100 | 100 | 100 | 100 | 100 |
| | A/B | 0.33 | 0.49 | 0.67 | 1.00 | 0.00 | 0.00 | 0.00 | | | 0.65 |
| | (A + B)/C | | | | | 0.65 | 0.99 | 0.42 | 0.42 | 0.15 | |
| | (A + B + C)/D | 4.36 | 3.31 | 2.73 | 2.18 | 6.89 | 8.35 | 5.95 | 2.28 | 3.06 | 2.77 |
| | scum adhesive property | C | C | C | B | C | C | C | C | C | C |
| | foam removal property | A | A | A | A | A | A | A | C | B | A |
| | scum hydrophilicity | C | C | C | C | B | B | B | A | A | A |

(4) Foam Fineness Test

The contents of Examples 1-23 and Comparative Examples 1-10 shown in Table 1 were prepared by a conventional method, and then diluted 5-fold with ion exchange water. Thereafter, the diluted product (10 g) was weighed in a 30 mL glass vial and used as a sample. After the sample was sufficiently foamed by shaking up and down for not less than 5 seconds, the appearance was evaluated according to the following criteria, and the degree of fineness of the foam was evaluated according to the following criteria. Finer foam contributes to improved satisfaction during use and production of abundant foam volume. The results are shown in Table 2.
A: fine
B: rather fine
C: crude (5) Refreshing Feeling Evaluation The contents of Examples 1-23 and Comparative Examples 1-10 shown in Table 1 were prepared by a conventional method, and then diluted 5-fold with ion exchange water. Thereafter, three professional panelists washed their hands well with the diluted product (10 g) and rinsed with tap water. After sufficiently drying, they evaluated refreshing feeling according to the following criteria. A strong refreshing feeling not only improves satisfaction during use, but also clears the end of rinsing, thus contributing to the reduction of rinsing water after body washing and shortening of the rinsing time. The results are shown in Table 2.
A: very refreshing
B: refreshing
C: less refreshing

TABLE 2

| | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 |
|---|---|---|---|---|---|---|---|---|---|---|---|---|
| refreshing feeling | B | B | A | A | A | B | B | A | A | A | A | B |
| fineness of foam | A | A | A | A | A | A | A | A | A | A | A | A |

TABLE 2-continued

|  | Ex. 13 | Ex. 14 | Ex. 15 | Ex. 16 | Ex. 17 | Ex. 18 | Ex. 19 | Ex. 20 | Ex. 21 | Ex. 22 | Ex. 23 |
|---|---|---|---|---|---|---|---|---|---|---|---|
| refreshing feeling | A | A | A | A | A | B | A | A | A | A | A |
| fineness of foam | A | A | A | A | A | A | A | A | A | A | A |

|  | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 | Comp. Ex. 10 |
|---|---|---|---|---|---|---|---|---|---|---|
| refreshing feeling | C | C | C | C | C | C | C | C | C | C |
| fineness of foam | C | C | C | C | B | B | B | B | B | C |

[Preparation 2 of Composition]

Each component described in Tables 3-5 was mixed and adjusted to pH 9.0 with citric acid or potassium hydroxide to prepare a liquid cleansing agent for body. The unit of the compositions shown in Tables 3-5 is wt %.

Potassium lauroylglycyl glycinate and potassium myristoylglycyl glycinate can be prepared by the Schotten-Baumann method and the like of acid chloride and glycine derived from potassium lauroyl glycinate or potassium myristoyl glycinate.

The potassium lauroylglutamyl glutamate was prepared by synthesizing by the Schotten-Baumann method using glutamylglutamic acid and long-chain fatty acid chloride, followed by purification.

[Preparation 1 of Cleansing Composition]

TABLE 3

| starting material name | trade name | amount |
|---|---|---|
| potassium lauroyl glycinate |  | 3.8 |
| potassium lauroylglycyl glycinate |  | 1.0 |
| potassium myristoyl glycinate |  | 5.7 |
| potassium myristoylglycyl glycinate |  | 1.4 |
| potassium lauroyl glutamate |  | 6.4 |
| potassium lauroylglutamyl glutamate |  | 1.6 |
| cocamidopropyl betaine (30%) | Softazline CPB (30%) | 30.0 |
| potassium laurate |  | 5.0 |
| potassium myristate |  | 5.0 |
| cocamide DEA | Amizol CDE | 3.6 |
| butylene glycol |  | 3.0 |
| glycol distearate | Emalex EG-di-SE | 2.0 |
| lauroyl arginine |  | 0.01 |
| potassium hydroxide |  | to pH 9.0 |
| water |  | balance |
| preservative |  | q.s. |
| flavor |  | q.s. |
| total weight % |  | 100.0 |

The obtained cleansing composition was superior in foam removal and suppressed formation of scum compared to the cleansing compositions obtained by the conventional method.

[Preparation 2 of Cleansing Composition]

TABLE 4

| starting material name | trade name | amount |
|---|---|---|
| sodium laureth sulfate (70%) | Emal 270J | 12.9 |
| cocamidopropyl betaine (30%) | Mirataine BET C-30 | 15.0 |

TABLE 4-continued

| starting material name | trade name | amount |
|---|---|---|
| potassium lauroyl glycinate |  | 0.8 |
| potassium lauroylglycyl glycinate |  | 0.2 |
| potassium myristoyl glycinate |  | 1.4 |
| potassium myristoylglycyl glycinate |  | 0.4 |
| potassium lauroyl glutamate |  | 1.5 |
| potassium lauroylglutamyl glutamate |  | 0.3 |
| cocamide DEA | Amizol CDE | 2.0 |
| potassium laurate |  | 1.1 |
| potassium myristate |  | 1.3 |
| sodium pyrrolidone carboxylate | AJIDEW NL-50 (50%) | 2.0 |
| sodium chloride |  | 0.5 |
| lauroyl arginine |  | 0.01 |
| preservative |  | as appropriate |
| purified water |  | balance |
| flavor |  | as appropriate |
| potassium hydroxide |  | to pH 9.0 |
| total weight % |  | 100.0 |

The obtained cleansing composition was superior in foam removal and suppressed formation of scum compared to the cleansing compositions obtained by the conventional method.

[Preparation 3 of Cleansing Composition]

TABLE 5

| starting material name | trade name | amount |
|---|---|---|
| lauric acid | NAA-122 | 6.9 |
| myristic acid | NAA-142 | 3.4 |
| palmitic acid | NAA-160 | 0.7 |
| stearic acid | NAA-180 | 0.7 |
| cocamidopropyl betaine | Amphitol 55AB | 6.6 |
| potassium lauroyl glycinate |  | 5 |
| potassium lauroylglycyl glycinate |  | 0.5 |
| potassium myristoyl glycinate |  | 7.5 |
| potassium myristoylglycyl glycinate |  | 0.7 |
| potassium lauroyl glutamate |  | 1.5 |
| potassium lauroylglutamyl glutamate |  | 0.05 |
| propylene glycol | propylene glycol for cosmetic | 1 |
| glycerol | Kao Corporation concentrated glycerol | 2.5 |
| potassium glutamate |  | 0.2 |
| glycine |  | 2 |
| glycylglycine |  | 0.5 |
| hydroxypropylmethylcellulose | Metolose 90SH-4000 | 1 |

TABLE 5-continued

| starting material name | trade name | amount |
|---|---|---|
| guar hydroxypropyltrimonium chloride | Jaguar Excel | 0.5 |
| glycol distearate | Emalex Eg-Di-SE | 1 |
| lauroyl arginine | Amisafe AL-01 | 0.01 |
| potassium chloride | | 0.5 |
| potassium hydroxide | | 3.4 to pH 9.0 |
| citric acid | | |
| water | | balance |
| total (weight %) | | 100 |

The obtained cleansing composition was superior in foam removal and suppressed formation of scum compared to the cleansing compositions obtained by the conventional method.

INDUSTRIAL APPLICABILITY

The present invention can provide a cleansing agent that is superior in foam removal and suppresses formation of scum.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A composition, comprising:
(A) N-lauroyl glycine or a salt thereof;
(B) N-myristoyl glycine or a salt thereof; and
(C) N-lauroyl glutamic acid or a salt thereof,
wherein
a weight ratio of (A)/(B) is 0.3 to 2.3,
a weight ratio of ((A)+(B))/(C) is 0.1 to 9,
and a total weight of (A), (B), and (C) is 15 to 40 wt %, relative to the total weight of the composition.

2. The composition according to claim 1, further comprising:
(D) at least one fatty acid having 6 to 24 carbon atoms or a salt thereof.

3. The composition according to claim 2, wherein said at least one fatty acid having 6 to 24 carbon atoms or a salt thereof (D) is at least one selected from the group consisting of octanoic acid, a sodium salt of octanoic acid, a potassium salt of octanoic acid, a triethanolamine salt of octanoic acid, decanoic acid, a sodium salt of decanoic acid, a potassium salt of decanoic acid, a triethanolamine salt of decanoic acid, lauric acid, a sodium salt of lauric acid, a potassium salt of lauric acid, a triethanolamine salt of lauric acid, myristic acid, a sodium salt of myristic acid, a potassium salt of myristic acid, a triethanolamine salt of myristic acid, palmitic acid, a sodium salt of palmitic acid, a potassium salt of palmitic acid, a triethanolamine salt of palmitic acid, stearic acid, a sodium salt of stearic acid, a potassium salt of stearic acid, and a triethanolamine salt of stearic acid.

4. The composition according to claim 2, wherein a weight ratio of ((A)+(B)+(C)/(D) is 1.0 to 10.

5. A method of cleaning hair, skin, dishware, cookware, or clothes, comprising contacting hair, skin, dishware, cookware, or clothes with a composition according to claim 2,
wherein said at least one fatty acid having 6 to 24 carbon atoms or a salt thereof (D) is present in said composition in an amount of not less than 0.1 wt % and not more than 50 wt % relative to the total weight of said cleansing composition.

6. The method according to claim 5, wherein said at least one fatty acid having 6 to 24 carbon atoms or a salt thereof (D) is present in said composition in an amount of not less than 0.5 wt % and not more than 30 wt % relative to the total weight of said cleansing composition.

7. The method according to claim 5, wherein said skin is facial skin.

8. The composition according to claim 2, wherein said at least one fatty acid having 6 to 24 carbon atoms or a salt thereof (D) is at least one selected from the group consisting of lauric acid, a sodium salt of lauric acid, a potassium salt of lauric acid, and a triethanolamine salt of lauric acid.

9. The composition according to claim 2, wherein said at least one fatty acid having 6 to 24 carbon atoms or a salt thereof (D) is a potassium salt of lauric acid.

10. The composition according to claim 1, wherein said N lauroyl glutamic acid or salt thereof (C) is a salt with at least one selected from the group consisting of sodium, potassium, and triethanolamine.

11. The composition according to claim 1, wherein said N-lauroyl glycine or salt thereof (A) is a salt with at least one selected from the group consisting of sodium, potassium and triethanolamine.

12. The composition according to claim 1, wherein said N-myristoyl glycine or salt thereof (B) is a salt with at least one selected from the group consisting of sodium, potassium, and triethanolamine.

13. The composition according to claim 1, further comprising:
(E) N-lauroylglycyl glycine or a salt thereof.

14. The composition according to claim 1, further comprising:
(F) N-myristoylglycyl glycine or a salt thereof.

15. The composition according to claim 1, further comprising:
(G) N-lauroylglutamyl glutamic acid or a salt thereof.

16. The composition according to claim 1, further comprising:
(H) at least one N-acyl arginine or a salt thereof.

17. The composition according to claim 1, wherein a weight ratio of ((A)+(B))/(C) is 0.5 to 4.

18. The composition according to claim 1, wherein a total weight of (A), (B), and (C) is 20 to 30 wt % relative to the total weight of said composition.

19. A method of cleaning hair, skin, dishware, cookware, or clothes, comprising contacting hair, skin, dishware, cookware, or clothes with a composition according to claim 1.

20. The method according to claim 19, wherein said skin is facial skin.

* * * * *